United States Patent [19]
You

[11] Patent Number: 6,004,754
[45] Date of Patent: Dec. 21, 1999

[54] **DNA SEQUENCE, RELATED PROBES AND PRIMERS FOR THE DETECTION OF *STREPTOCOCCUS AGALACTIAE***

[75] Inventor: Qimin You, Lutherville, Md.

[73] Assignee: Becton Dickinson and Company, Franklin Lakes, N.J.

[21] Appl. No.: 09/010,310

[22] Filed: Jan. 21, 1998

[51] Int. Cl.$^6$ .............................. C12Q 1/68; C12P 19/34; C07H 21/00; C07H 21/02
[52] U.S. Cl. ........................... 435/6; 435/91.1; 435/91.2; 536/23.1; 536/24.3; 536/24.32
[58] Field of Search ............................ 435/6, 91.1, 91.2; 536/23.1, 24.3, 24.31, 24.32, 24.33

[56] References Cited

U.S. PATENT DOCUMENTS

| | | | |
|---|---|---|---|
| 5,620,847 | 4/1997 | Greisen et al. | 435/6 |
| 5,631,147 | 5/1997 | Lohman et al. | 435/91.2 |

OTHER PUBLICATIONS

Walker T. PCR Meth. and Appl. pp.1–6, 1993.

Baker, Carol J., Group B Streptococcal Infection in Newborns; *New Eng. J. Med.*, 314, pp. 1702–1704 (1996).

Daly, Judy A. et al., Use of Rapid, Nonradioactive DNA probes in Culture Confirmation Tests to Detect*Streptococcus agalactiae, Haemophilus influenzae*, and Enterococcus spp, from Pediatric Patients with Significant Infections; *J. of Clin. Microbio.*, 29, pp. 80–82 (1991).

Baseggio, Nina et al., Strain differentiation of isolates of streptococci from bovine mastitis by pulsed–field gel electrophoresis; *Mol. and Cel. Probes*, 11, pp. 349–354 (1997).

Baker, Carol J., Summary of the Workshop on Perinatal Infectins Due to Group B Streptococcus; *J. of Infect. Diseases*; 136, pp. 137–152 (1977).

Chatellier, Sonia et al., Characterization of *Streptococcus agalactiae*Strains by Randomly Amplified Polymorphic DNA Analysis; *J. of Clin. Microbiol.*; 35, pp. 2573–2579 (1997).

Baker, Carol J.; Correlation of Maternal Antibody Deficiency with Susceptibility to Neonatal Group B Streptococcal Infection; *New Eng. J. of Med.*, 294, pp. 753–756 (1976).

Morales, Walter J.; Reduction of group B streptococcal maternal and neonatal infections in preterm pregnancies with premature rupture of membranes through a rapid identification test; *Am. J. of Obstet. Gynecol.*, 157, pp. 13–16 (1987).

*Primary Examiner*—Kenneth R. Horlick
*Assistant Examiner*—Jeffrey Siew
*Attorney, Agent, or Firm*—David W. Highet, Esq.

[57] ABSTRACT

Disclosed herein is newly-identified DNA sequence from *Streptococcus agalactiae* ("GBS") designated GBS3.1. Also disclosed are methods, oligonucleotide probes, amplification primers, and kits for the species-specific detection of *S. agalactiae*. Preferably, *S. agalactiae* is detected by amplifying the *S. agalactiae* nucleic acids using the disclosed amplification primers, and then detecting the amplified nucleic acids. In a more preferred embodiment, *S. agalactiae* nucleic acids are amplified and detected by thermophilic strand displacement amplification (tSDA).

35 Claims, 5 Drawing Sheets

FIG-1   GBS3.1 SEQUENCE (SEQ ID NO:3):

```
AAGCAATTCA GATCATTTTT CAGTAACGGT GGAACGTTTA CCTAGAACCC       50
ATTATACTGC TAGCCTTGAA GGGACTAGTG ACGGAAAAGA GATTAAACTC      100
AAAAAGATT ATGATGGTAA AAACCAAACT ATTGATTTAT CGGTCGCTTT       150
TAAATCTTTT ACAGTAACAA GTAATCTTAT GGATGGTAAT CTTTATTTTG      200
GTGATAATCG TATTGCTAAA TTAAAAGATG GTAGCTATTC CGTAGAGAAT      250
TATCCAGTGA CTGATGGTTC AAAAGCTTAT ATCAAAAAAG TTTTTAATGA      300
TGGTGAGATA ACCTCTCATA AACAAAAATT AATCTC                     336
```

FIG-2A SEQUENCE ALIGNMENT OF GBS3.1 FRAGMENTS

GBS 15 Strain Formatted Alignment

FIG-2B SEQUENCE ALIGNMENT OF GBS3.1 FRAGMENTS

FIG-3A

Primers

| | | |
|---|---|---|
| GBS3.1AL48: | 5' CGA TTC CGC TCC AGA CTT CTC GGG AGT AAC GGT GGA ACG T 3' | (SEQ ID NO:10) |
| GBS3.1AL46: | 5' CGA TTC CGC TCC AGA CTT CTC GGG AGT AAC GGT GGA ACG 3' | (SEQ ID NO:11) |
| GBS3.1AL42: | 5' CGA TTC CGC TCC AGA CTT CTC GGG AGT AAC GGT GGA AC 3' | (SEQ ID NO:12) |
| GBS3.1AR46: | 5' ACC GCA TCG AAT GCA TGT CTC GGG GTC ACT AGT CCC TTC A 3' | (SEQ ID NO:13) |
| GBS3.1AR44: | 5' ACC GCA TCG AAT GCA TGT CTC GGG GTC ACT AGT CCC TTC 3' | (SEQ ID NO:14) |
| GBS3.1AR42: | 5' ACC GCA TCG AAT GCA TGT CTC GGG TCA CTA GTC CCT TCA 3' | (SEQ ID NO:15) |

Bumpers

| | | |
|---|---|---|
| GBS3.1BL44: | 5' AAG CAA TTC AGA TCA TT 3' | (SEQ ID NO:16) |
| GBS3.1BR44: | 5' TTT GAG TTT AAT CTC TTT 3' | (SEQ ID NO:17) |

Detectors

| | | |
|---|---|---|
| GBS3.1D40: | 5' GTT TAC CTA GAA CC 3' | (SEQ ID NO:18) |
| GBS3.1DR46: | 5' TGG GTT CTA GGT AAA C 3' | (SEQ ID NO:19) |
| GBS3.1C42: | 5' TTA TAC TGC TAG CCT 3' | (SEQ ID NO:20) |

FIG-3B THE SELECTED GBS3.1 tSDA SYSTEM:

```
         GBS3.1BL44              GBS3.1AL48             GBS3.1DR46                        GBS3.1C42              GBS3.1AR46                      GBS3.1BR44
AAGCAATTCAGATCATTTTCAGTAACGGTGAACGTTTACCTAGAACCATTATACTGCTAGCCTTGAAGGACTAGTGACGGAAAAGAGATTAAACTC AAA
                                                       GBS3.1D40
```

DNA SEQUENCE, RELATED PROBES AND PRIMERS FOR THE DETECTION OF STREPTOCOCCUS AGALACTIAE

FIELD OF THE INVENTION

The present invention relates to methods for identifying microorganisms, in particular methods and nucleic acid sequences for identifying Streptococcus agalactiae by nucleic acid amplification and nucleic acid hybridization.

BACKGROUND OF THE INVENTION

Streptococcus agalactiae, also known as Group B Streptococcus ("GBS") has long been associated with mastitis in dairy animals. More recently, GBS has been recognized as a serious pathogenic agent in humans; GBS is a causative agent in meningitis, bacteremia, endocarditis, bronchopneumonia, arthritis, peritonitis, wound infections, and urinary tract infections in adults. Furthermore, GBS is one of the leading causes of neonatal and maternal morbidity and mortality. As there is almost complete identity in GBS serotypes isolated from mothers and their infected newborns, it appears that GBS is transmitted from the maternal genital tract to the neonate as it passes through the birth canal. This is a significant source of pathogenic infection for newborns; it is estimated that between 5 % and 30% of pregnant women are infected with GBS. The mortality rate in neonates affected with GBS is 20–25%, with 30% of the infected neonates developing meningitis. Baker, N. Engl. J. Med. 314, 1702 (1986). In addition, GBS accounts for approximately 20% of cases of post-partum endometriosis. Id.

Conventional methods of identifying GBS include gram staining, hemolysis, serological classification on the basis of the Group B antigens, hippurate hydrolysis, the CAMP test, and reaction to bacitracin and sulfamethoxazole-trimethoprim disks. Daly et al., J. Clin. Microbiology 29, 80 (1991). These methods all suffer from low-sensitivity, variable accuracy, and a long turn-around time. Rapid identification of GBS is desirable, especially at the time of parturition, so that both mother and infant can receive prophylactic treatment, thereby preventing the onset of maternal or neonatal disease.

Nucleic acid based diagnostic assays, such as Southern hybridization, offer rapid means of identifying microorganisms, usually in less than one day. Polymerase chain reaction (PCR)-based methods are even more sensitive and can sometimes provide results within hours. However, nucleic acid based methodologies are often fraught with drawbacks. Most of these methods are costly, are available for only a few species of microorganisms, and can resolve only one species per sample tested. Moreover, nucleic acid based assays require the development of oligonucleotide probes or primers that are specific for the microorganism of interest.

To obviate the problems attendant to conventional diagnosis of GBS, there have been attempts to develop nucleic acid based diagnostic methods of identifying GBS.

Baseggio et al., Mol. Cell Probes 11, 349 (1997), provides a method for classifying strains of GBS isolated from mastitic dairy cattle. Genomic DNA isolated from GBS isolates from infected animals is subjected to restriction digestion followed by pulsed-field gel electrophoresis. The electrophoretic profiles of the restriction digests are characteristic for different strains of GBS and provide the basis for diagnosis.

Daly et al., J. Clin. Microbiology 29, 80 (1991), discloses the use of a chemiluminescent-labeled oligonucleotide probe (ACCUPROBE™; Gen-Probe, Inc.) to identify GBS. The DNA probe is targeted to a region of the GBS rRNA. The assay involves hybridizing the probe to target RNA by in-solution hybridization, and then measuring the chemiluminescence. This assay suffers from a low-sensitivity because the target nucleic acids are not amplified prior to hybridization. The infectious microorganisms must be cultured to produce isolated colonies to obtain adequate target rRNA for analysis.

Chatellier et al., J. Clin. Microbiology 35, 2573 (1997), concerns a method for identifying GBS strains in cerebrospinal fluid samples by a randomly-amplified polymorphic DNA (RAPD) assay. Target DNA is amplified by PCR using single primers of random oligonucleotide sequence. The PCR amplification products are separated by electrophoreses, and the resulting gel banding patterns are characteristic of particular GBS strains and are used to make a diagnosis.

U.S. Pat. No. 5,620,847 to Greisen et al. also teaches a PCR-based method for identifying GBS in cerebrospinal fluid. In the first step, a universal bacterial primer is used to amplify a target region in the 16S rRNA. The amplified nucleic acids are then analyzed with a panel of probes, one of which distinguishes GBS from other bacterial species found in cerebrospinal fluid.

Notwithstanding the investigations described above, there remains a need in the art for rapid, accurate and sensitive methods for the identification of GBS.

SUMMARY OF THE INVENTION

The present invention provides a newly-identified region of the Streptococcus agalactiae ("GBS") genome that can be used to detect S. agalactiae nucleic acids by hybridization or amplification assays. Nucleic acid probes and amplification primers have been developed that result in the species-specific identification of S. agalactiae without detectable cross-reactivity with non-GBS species.

As a first aspect, the present invention provides a method for species-specific detection of Streptococcus agalactiae nucleic acids comprising the steps of: (a) hybridizing an oligonucleotide probe to Streptococcus agalactiae nucleic acids, the probe consisting of at least 10 consecutive nucleotides of a Streptococcus agalactiae GBS3.1 sequence; and then (b) detecting hybridization between the oligonucleotide probe and the Streptococcus agalactiae nucleic acids.

As a second aspect, the present invention provides a method for species-specific detection of Streptococcus agalactiae nucleic acids comprising the steps of: (a) hybridizing to Streptococcus agalactiae nucleic acids at least one amplification primer comprising a target binding sequence, the target binding sequence consisting of at least 10 consecutive nucleotides of a Streptococcus agalactiae GBS3.1 sequence; and (b) amplifying the Streptococcus agalactiae nucleic acids; and then (c) detecting the amplified Streptococcus agalactiae nucleic acids. In preferred embodiments, the amplification primer contains sequences for amplification of the target nucleic acids. In more preferred embodiments, the target nucleic acids are amplified by thermophilic strand displacement amplification (tSDA).

As a third aspect, the present invention provides a method for species-specific detection of Streptococcus agalactiae nucleic acids, comprising the steps of: (a) hybridizing to Streptococcus agalactiae nucleic acids a first and a second amplification primer, the target binding sequence of each amplification primer consisting of at least 10 consecutive nucleotides of a Streptococcus agalactiae GBS3.1 sequence, wherein the first and second amplification primers are selected such that the first and second amplification primers are adjacent and ligatable when hybridized to the *Streptococcus agalactiae* nucleic acids; and (b) ligating the hybridized first and second amplification primers to produce an amplification product; and then (c) detecting the amplification product.

As a fourth aspect, the present invention discloses isolated DNA consisting of a *Streptococcus agalactiae* GBS3.1 sequence. In preferred embodiments the GBS3.1 sequence is selected from the group consisting of SEQ ID NO:3, SEQ ID NO:6, SEQ ID NO:7, SEQ ID NO:8, and SEQ ID NO:9. Further disclosed are oligonucleotide probes and amplification primers comprising a target binding sequence consisting of at least 10 consecutive nucleotides of a GBS3.1 sequence. Preferably, the oligonucleotide has a sequence selected from the group consisting of SEQ ID NO:4, SEQ ID NO:5, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, the target binding sequence of SEQ ID NO: 15, SEQ ID NO:16, SEQ ID NO:17, SEQ ID NO:18, SEQ ID NO:19, and SEQ ID NO:20. In other preferred embodiments, the oligonucleotide further comprises a sequence for amplification of a target nucleic acid, and more preferably the oligonucleotide is selected from the group consisting of SEQ ID NO:10, SEQ ID NO:11, SEQ ID NO:12, SEQ ID NO:14, and SEQ ID NO:15.

As a fifth aspect, the present invention provides a set of primers for species-specific amplification of *Streptococcus agalactiae* nucleic acids comprising a first amplification primer comprising a target binding sequence consisting of at least 10 consecutive nucleotides of an isolated GBS3.1 sequence. Preferably, the first amplification primer is selected from the group consisting of SEQ ID NO:4, SEQ ID NO:5, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, the target binding sequence of SEQ ID NO:15, SEQ ID NO:16, SEQ ID NO:17, SEQ ID NO:18, SEQ ID NO:19, and SEQ ID NO:20. In alternate embodiments, the first amplification primer further comprises a sequence for amplification of the target nucleic acids. According to this embodiment, the first amplification primer is preferably selected from the group consisting of SEQ ID NO:10, SEQ ID NO:11, SEQ ID NO:12, SEQ ID NO:13, SEQ ID NO:14, and SEQ ID NO:15. Further disclosed are kits for species-specific detection of *Streptococcus agalactiae* nucleic acids comprising the inventive oligonucleotide probes and primers.

As a sixth aspect, the present invention provides a primer set for species-specific amplification of *Streptococcus agalactiae* nucleic acids comprising a first amplification primer consisting of SEQ ID NO:10, a second amplification primer consisting of SEQ ID NO:13, a first bumper primer consisting of SEQ ID NO:16, and a second bumper primer consisting of SEQ ID NO:17.

These and other aspects of the present invention are described in more detail in the description of the invention set forth below.

BRIEF DESCRIPTION OF THE DRAWINGS

FIG. 1 represents one strand of the GBS3.1 DNA sequence (SEQ ID NO:3) from type III GBS.

FIG. 2 shows the alignment of the GBS3.1 sequences from 15 GBS strains. Only 4 distinct sequences (SEQ ID NO:3 and SEQ ID NO:7, SEQ ID NO:8, SEQ ID NO:9) are represented by the 15 GBS strains. The GBS3.1 consensus sequence (SEQ ID NO:6) is indicated at the top of the alignment.

FIG. 3A and B shows the tSDA primers, bumpers and detectors of the GBS3.1 tSDA system and their targets in the GBS3.1 sequence.

FIG. 3A presents the sequences of the GBS3.1 tSDA amplification primers (SEQ ID NO:10, SEQ ID NO:11, SEQ ID NO:12, SEQ ID NO:13, SEQ ID NO:14, SEQ ID NO:15), bumpers (SEQ ID NO:16 and SEQ ID NO:17), and detectors (SEQ ID NO:18, SEQ ID NO:19, SEQ ID NO:20). The target binding sequences and the Bso B1 sites of the amplification primers are indicated by underlining and italics, respectively.

FIG. 3B shows the GBS3.1 tSDA system chosen for further study. This set of primers and bumpers target a region spanning nucleotides 1 to 103 of the GBS3.1 sequence and results in a 61 bp amplification product.

DETAILED DESCRIPTION OF THE INVENTION

Nucleotide sequences are presented herein by single strand only in the 5' to 3' direction, from left to right. Nucleotides are represented herein in the manner recommended by the IUPAC-IUB Biochemical Nomenclature Commission, in accordance with 37 C.F.R. § 1.822 and established usage.

The production and use of cloned genes, recombinant DNA, vectors, transformed host cells, selectable markers, proteins, and protein fragments by genetic engineering are well-known to those skilled in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

Disclosed herein is a newly-identified region of the *S. agalactiae* ("GBS") genomic DNA, which has been designated "GBS3.1". The GBS3.1 sequence exhibits a high degree of homology across GBS strains. The GBS3.1 sequences disclosed herein find use in methods of detecting and diagnosing GBS. For example, these sequences can be used to design hybridization probes for use in conventional Southern or dot blot hybridizations, or to design amplification primers for use in nucleic acid amplification procedures, such as Polymerase Chain Reaction (PCR), Ligase Chain Reaction (LCR), Strand Displacement Amplification (SDA), or thermophilic Strand Displacement Amplification (tSDA). Also disclosed herein are oligonucleotides, methods and kits for detection, preferably species-specific detection, of GBS.

The GBS3.1 sequences disclosed herein include the sequences given as SEQ ID NO:3, SEQ ID NO:7, SEQ ID NO:8, and SEQ ID NO:9, and the complementary sequences thereof. As used herein, the term "GBS3.1 sequences" also encompasses GBS3.1 sequences from strains of GBS other than those specifically disclosed herein. Alternatively stated, GBS3.1 sequences of the present invention include the amplification products (i.e., amplicons) resulting from amplification of GBS nucleic acids with GBS3.1 specific amplification primers, such as SEQ ID NO:4 and SEQ ID NO:5. GBS3.1 sequences from strains of GBS other than those specifically disclosed herein will generally be at least about 75% homologous (and more preferably 80%, 85%, 90% or even 95% homologous) to a continuous segment of DNA found within the GBS3.1 sequences given herein as SEQ ID NO:3, SEQ ID NO:7, SEQ ID NO:8, and SEQ ID NO:9, and will be able to hybridize to GBS nucleic acids under conditions of high stringency, as defined below.

The GBS3.1 sequences of the present invention include sequences that hybridize under conditions of high stringency to GBS nucleic acids and are substantially homologous to the GBS3.1 sequences specifically disclosed herein, and particularly the GBS3.1 sequences disclosed herein as SEQ ID NO:3, SEQ ID NO:7, SEQ ID NO:8, and SEQ ID NO:9. This definition is intended to encompass natural allelic variations in the GBS3.1 sequence. As used herein, nucleotide sequences that are "substantially homologous" are at least 75%, and more preferably are 80%, 90% or even 95% homologous.

High stringency hybridization conditions that will permit homologous DNA sequences to hybridize to a DNA sequence as given herein are well known in the art. For example, hybridization of such sequences to DNA disclosed herein may be carried out in 25% formamide, 5×SSC, 5×Denhardt's solution, with 100 µg/ml of single stranded DNA, and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3 M NaCl, 0.03 M sodium citrate, 0.1% SDS at 60° C., or even 70° C. See Sambrook et al., MOLECULAR CLONING, A LABORATORY MANUAL (2d ed. 1989), herein incorporated by reference in its entirety. In general, GBS3.1 sequences which hybridize to the GBS3.1 sequences disclosed herein will be at least 75%, 80%, 85%, 90% or even 95% homologous or more with the GBS3.1 sequences disclosed herein.

Oligonucleotide hybridization probes are also aspects of the present invention. As used herein, the term "probe" indicates an oligonucleotide that hybridizes to a target sequence, typically to facilitate its detection. As used herein, a "target sequence" refers to a nucleic acid sequence to which the probe specifically binds. Unlike a primer, a probe is not extended by a polymerase. The probe is often linked (directly or indirectly) to a detectable label to facilitate detection or capture when hybridized to the target sequence.

The probes disclosed herein hybridize to GBS3.1 nucleic acids. Typically, the probes of the present invention will hybridize to consecutive nucleotides of the GBS3.1 sequences disclosed herein under stringent conditions, as defined above. Alternatively stated, probes of the present invention will be at least 75%, 80%, 85%, 90% or even 95% homologous or more with consecutive nucleotides within the GBS3.1 sequences disclosed herein, in particular SEQ ID NO:3, SEQ ID NO:7, SEQ ID NO:8, and SEQ ID NO:9. In particular embodiments of the invention, the probes have nucleotide sequences as given herein as SEQ ID NO:4, SEQ ID NO:5, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, the target binding sequence of SEQ ID NO:15, SEQ ID NO:16, SEQ ID NO:17, SEQ ID NO:18, SEQ ID NO:19, and SEQ ID NO:20, and complementary sequences thereof.

As nucleic acids do not require complete homology to hybridize, it will be apparent to those skilled in the art that the probe sequences specifically disclosed herein may be modified so as to be substantially homologous to the probe sequences disclosed herein without loss of utility as GBS probes. It is well-known in the art that hybridization of homologous and partially homologous nucleic acid sequences may be accomplished by adjusting the hybridization conditions to increase or decrease the stringency (i.e., adjusting the hybridization temperature or salt content of the buffer).

Hybridization probes can be of any suitable length. There is no particular lower or upper limits to the length of the probe, as long as the probe hybridizes to the target GBS3.1 nucleic acids and functions effectively as a probe (e.g., facilitates detection). In one preferred embodiment of the invention the probe comprises at least 10 consecutive nucleotides of a GBS3.1 sequence, as defined above. The probes of the present invention can be at short as 50, 40, 30, 20, 15, or 10 nucleotides, or shorter. Likewise, the probes can be as long as 20, 40, 50, 60, 75, 100 or 200 nucleotides, or longer. The maximum length of the probe is the length of the particular GBS3.1 sequence selected. For example, a probe derived from the type III GBS sequence (see FIG. 1; SEQ ID NO:3) can be as long as 336 nucleotides.

In a preferred embodiment, the probe is species-specific, meaning that under stringent conditions (as defined above, e.g., a wash stringency of 0.3 M NaCl, 0.03 M sodium citrate, 0.1% SDS at 60° C.) it hybridizes only to nucleic acids from GBS and does not hybridize to nucleic acids from any non-GBS species, or does so to a negligible extent, such that there is only insignificant hybridization or detection of non-GBS nucleic acids. Alternately stated, a GBS-specific probe does not hybridize to or detect non-GBS nucleic acids (or does so to only an insignificant extent) under the same conditions in which the probe does hybridize to and detect GBS nucleic acids.

Another aspect of the present invention is a method for detecting GBS using a GBS3.1 probe, as defined above. According to this embodiment of the invention, a nucleic acid probe is hybridized to GBS nucleic acids, and the hybridization between the probe and the GBS nucleic acids is then detected. A preferred embodiment of the invention is a species-specific (as defined above) method of detecting GBS using a hybridization probe.

Hybridization can be carried out under any suitable technique known in the art. Typically, hybridizations will be performed under conditions of high stringency. It will be apparent to those skilled in the art that hybridization conditions can be altered to increase or decrease the degree of hybridization, the level of specificity of the hybridization, and the background level of non-specific binding (i.e., by altering hybridization or wash salt concentrations or temperatures).

Similarly, detection of hybridization between the probe and the GBS nucleic acids can be carried out by any method known in the art. The probe may contain a detectable label that will indicate hybridization between the labeled probe and the GBS nucleic acids. The detectable label of the probe is a moiety that can be detected either directly or indirectly. For direct detection of the label, probes may be tagged with a radioisotope and detected by autoradiography. Alternatively, the probe may be tagged with a fluorescent moiety and detected by fluorescence, as is known in the art. As a further alternative, the probe may be indirectly detected by tagging with a label that requires additional reagents to render it detectable. Illustrative methods of indirect labeling include those utilizing chemiluminescence agents, enzymes that produce visible reaction products, and ligands (e.g., haptens, antibodies or antigens) that may be detected by binding to labeled specific binding partners (e.g., hapten binding to a labeled antibody). Ligand labels are also useful for solid phase capture of the oligonucleotide probe (i.e., capture probes). Exemplary labels include biotin (detectable by binding to labeled avidin or streptavidin) and enzymes, such as horseradish peroxidase or alkaline phosphatase (detectable by addition of enzyme substrates to produce a colored reaction product). Methods of labeling oligonucleotides are well known in the art.

GBS3.1 amplification primers are also encompassed by the present invention. An amplification primer is an oligonucleotide useful for amplification of a target sequence by extension of the oligonucleotide after hybridization to the target sequence, or by ligation of multiple oligonucleotides that are adjacent when hybridized to the target sequence. The oligonucleotide primers of the present invention are preferably used to detect GBS by amplification of GBS3.1 nucleic acid target sequences.

Copies of the target sequence which are generated during the amplification reaction are referred to as "amplification products", "amplimers", or "amplicons". An extension product refers to the copy of a target sequence produced by hybridization of a primer and extension of the primer by polymerase using the target sequence as a template.

As used herein, the "target sequence" of an amplification primer refers to a nucleic acid sequence to which the amplification primer specifically binds and amplifies. These include the original nucleic acid sequence to be amplified and its complementary second strand as well as either strand of a copy of the original target sequence generated during the amplification reaction. The portion of the primer that hybridizes to the target sequence (i.e., target binding sequence or annealing region) may also be used as a hybridization probe for detection of target GBS nucleic acids in various nucleic acid hybridization methods, as described in more detail above.

Thus, it will be apparent to those skilled in the art that primers and probes of the present invention are structurally similar or identical in many cases. The terms "primer" and "probe" refer to the function of the oligonucleotide. An oligonucleotide may function as a probe if it is hybridized to a target sequence to capture or detect the target sequence. Alternately, the same oligonucleotide may function as a primer if it is used to amplify the target, as described below.

Suitable bases for preparing the oligonucleotide probes or amplification primers of the present invention may be selected from naturally occurring nucleotide bases such as adenine, cytosine, guanine, uracil, and thymine; and non-naturally occurring or "synthetic" nucleotide bases such as 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, β,D-galactosylqueosine, 2'-O-methylguanosine, inosine, $N^6$-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, $N^6$-methyladenosine, 7-methylguanosine, 5-methylaminomethyluridine, 5-methoxyaminomethyl-2-thiouridine, β,D-mannosylqueosine, 5-methoxycarbonylmethyluridine, 5-methoxyuridine, 2-methylthio-$N^6$-isopentenyladenosine, N-((9-β-D-ribofuranosyl-2-methylthiopurine-6-yl)carbamoyl) threonine, N-((9-β-D-ribofuranosylpurine-6-yl)N-methylcarbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-β-D-ribofuranosylpurine-6-yl)carbamoyl)threonine, 2'-O-methyl-5-methyluridine, 2'-O-methyluridine, wybutosine, and 3-(3-amino-3-carboxypropyl)uridine.

Likewise, chemical analogs of oligonucleotides (e.g., oligonucleotides in which the phosphodiester bonds have been modified, e.g., to the methylphosphonate, the phosphotriester, the phosphorothioate, the phosphorodithioate, or the phosphoramidate) may also be employed. Protection from degradation can be achieved by use of a "3'-end cap" strategy by which nuclease-resistant linkages are substituted for phosphodiester linkages at the 3' end of the oligonucleotide. See Tidd and Warenius, *Br. J. Cancer* 60, 343 (1989); Shaw et al., *Nucleic Acids Res.* 19, 747 (1991). Phosphoramidates, phosphorothioates, and methylphosphonate linkages all function adequately in this manner. More extensive modification of the phosphodiester backbone has been shown to impart stability and may allow for enhanced affinity and increased cellular permeation of oligonucleotides. See Milligan, et al., *J. Med. Chem.* 36, 1923 (1993). Many different chemical strategies have been employed to replace the entire phosphodiester backbone with novel linkages. Id. Backbone analogues include phosphorothioate, phosphorodithioate, methylphosphonate, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene(methylimino)(MMI) or methyleneoxy(methylimino)(MOMI) linkages. Phosphorothioate and methylphosphonate-modifiedoligonucleotides are particularly preferred due to their availability through automated oligonucleotide synthesis. Id. The oligonucleotide may be a "peptide nucleic acid" such as described in Nielsen et al., *Science* 254, 1497 (1991). The only requirement is that the oligonucleotide probe should possess a sequence at least a portion of which is capable of binding to a portion of the sequence of a target DNA molecule.

The amplification primers disclosed herein hybridize to and amplify GBS3.1 nucleic acids. When a set of two or more amplification primers is used to amplify GBS3.1 nucleic acids, it is preferred that the set of amplification primers is contained in a common aqueous solution. Typically, amplification primers will hybridize to consecutive nucleotides of the GBS3.1 sequences disclosed herein under stringent conditions, as defined above. Alternatively stated, primers of the present invention will be at least 75%, 80%, 85%, 90% or even 95% homologous or more with consecutive nucleotides within the GBS3.1 sequences disclosed herein, in particular SEQ ID NO:3, SEQ ID NO:7, SEQ ID NO:8, and SEQ ID NO:9.

Amplification primers can be of any suitable length. There is no particular lower or upper limits to the length of the primer, so long as the primer hybridizes to the target GBS3.1 DNA and functions effectively as an amplification primer. In one preferred embodiment of the invention the primers comprise at least 10 consecutive nucleotides of a GBS3.1 sequence, as defined above. The primers can be as short as 50, 40, 30, 20, 15, or 10 nucleotides, or shorter. Likewise, the primers can be as long as 20, 40, 50, 60, 75, 100 or 200 nucleotides, or longer.

In a preferred embodiment of the invention, the amplification primer is species-specific, meaning that under stringent conditions (as defined above), the amplification primer hybridizes to, amplifies, and detects only GBS nucleic acids, and does not hybridize to, amplify, and detect nucleic acids from any non-GBS species, or does so to a negligible extent, such that there is only insignificant hybridization, amplification and detection of non-GBS nucleic acids. Alternately stated, a GBS-specific amplification primer does not hybridize to, amplify, and detect non-GBS nucleic acids (or does so to only an insignificant extent) under the same conditions in which the amplification primer does hybridize to, amplify, and detect GBS nucleic acids.

In particular embodiments of the present invention, the amplification primer or its target binding sequence has a sequence as given by SEQ ID NO:4, SEQ ID NO:5, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, the target binding sequence of SEQ ID NO:15, SEQ ID NO:16, SEQ ID NO:17, SEQ ID NO:18, SEQ ID NO:19, or SEQ ID NO:20. Alternatively, the amplification primer has a sequence as given by SEQ ID NO:10, SEQ ID NO:11, SEQ ID NO12:, SEQ ID NO:13, SEQ ID NO:14, or SEQ ID NO:15. Preferably, the amplification primer has sequence as given by SEQ ID NO:4, SEQ ID NO:5, SEQ ID NO:10, SEQ ID NO:11, SEQ ID NO:12, SEQ ID NO:13, SEQ ID NO:14, SEQ ID NO:15, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, or the target binding sequence of SEQ ID NO:15. More preferably, the amplification primer has a sequence as given by SEQ ID NO:4, SEQ ID NO:5, SEQ ID NO:10, or SEQ ID NO:13.

As nucleic acids do not require complete homology to hybridize, it will be apparent to those skilled in the art that the primer sequences specifically disclosed herein may be modified so as to be substantially homologous to the primer sequences disclosed herein without loss of utility as GBS amplification primers. It is well-known in the art that hybridization of homologous and partially homologous nucleic acid sequences may be accomplished by adjusting the hybridization conditions to increase or decrease the stringency (i.e., adjusting the hybridization temperature or salt content of the buffer).

The inventive amplification primers disclosed herein can be used in any method of nucleic acid amplification known in the art. Such methods include but are not limited to Polymerase Chain Reaction (PCR; described in U.S. Pat. Nos. 4,683,195, 4,683,202, 4,800,159, 4,965,188), Strand Displacement Amplification (SDA; described by Walker et al., Proc. Nat. Acad. Sci. USA 89, 392 (1992), herein incorporated by reference in its entirety; Walker et al., Nucl. Acids Res. 20, 1691 (1992), herein incorporated by reference in its entirety; U.S. Pat. No. 5,270,184), thermophilic Strand Displacement Amplification (tSDA; U.S. Pat. No. 5,648,211 and European Patent Application No. EP 0 684 315 to Frasier et al.), Self-Sustained Sequence Replication (3SR; J. C. Guatelli et al., Proc Natl. Acad. Sci. USA 87, 1874 (1990)), Nucleic Acid Sequence-Based Amplification (NASBA; U.S. Pat. No. 5,130,238 to Cangene), the Qβ replicase system (P. Lizardi et al., BioTechnology 6, 1197 (1988)), or transcription based amplification (D. Y. Kwoh et al., Proc. Natl. Acad. Sci. USA 86, 1173 (1989)). Preferably, the amplification primers of the present invention are used to carry out SDA or tSDA, with tSDA being more preferred.

For amplification by tSDA (or SDA), the oligonucleotide primers are preferably selected such that the GC content is low, preferably less than 70% of the total nucleotide composition of the probe. Similarly, for tSDA the target sequence preferably has a low GC content to minimize secondary structure. An amplification primer for use in tSDA comprises a target binding sequence, a recognition site for a restriction endonuclease, and a tail. The target binding sequence is at the 3' end of the tSDA amplification primer. It hybridizes to the 3' end of the target sequence.

The target binding sequence confers hybridization specificity on the amplification primer. A recognition site for a restriction endonuclease is 5' of the target binding sequence. The restriction endonuclease is one that will nick one strand of a DNA complex when the recognition site is hemimodified, as described by Walker et al. Proc. Nat'l Acad. Sci. USA 89, 392 (1992); Nucl. Acids. Res. 20, 1691 (1992); both publications are herein incorporated by reference in its entirety. The tail of the amplification primer is comprised of the nucleotides 5' of the restriction endonuclease recognition site. The length and sequence of the tail are generally not critical. The tail functions as a polymerase repriming site when the remainder of the amplification primer is nicked and displaced during tSDA.

As used herein, a "bumper primer" or "external primer" is a primer used to displace primer extension products. The bumper primer hybridizes to a target sequence upstream of the amplification primer target binding sequence such that extension of the bumper primer displaces the downstream amplification primer and its extension product. Generally, it will not be necessary that the bumper primers used in SDA and tSDA reactions be GBS-specific. The bumper primers are only required to hybridize to their targets upstream from the amplification primers, so that when the bumper primers are extended they will displace the amplification primer and its extension product. The sequence of the bumper primers is therefore generally not critical, and may be derived from any upstream target sequence that is sufficiently close to the binding site of the amplification primer to allow displacement of the amplification primer extension product upon extension of the bumper primer. Occasional mismatches with the target in the bumper primer sequence or some cross-hybridization with non-target sequences do not generally have a negative effect on amplification efficiency as long as the bumper primer still hybridizes to the specific target sequence. Extension of bumper primers is one method for displacing the extension products of amplification primers, but heating is also suitable. In one embodiment of the invention, bumpers comprise at least 10 consecutive nucleotides of a GBS3.1 sequence, as defined above. In preferred embodiments, one or more of the bumper primers have sequences as given herein by SEQ ID NO:16 and SEQ ID NO:17. Bumper primers may also be used as the target binding sequence of an amplification primer or as a hybridization probe, each as defined above.

For amplification methods that do not require specialized sequences at the ends of the target (e.g., PCR and LCR), the amplification primer typically consists essentially of only the target binding sequence. In the case of amplification methods that require primers containing specialized sequences in addition to the target-binding sequence, the specialized sequence may be linked to the target binding sequence using routine methods for preparation of oligonucleotides without altering the hybridization specificity of the target binding sequence. Illustrative examples of amplification methods requiring specialized primer sequences for amplification include: SDA and tSDA, 3SR, NASBA, and transcription based amplification. These specialized sequences do not hybridize to the target nucleic acids, but instead perform a separate function, which is required for amplification (e.g., the restriction enzyme site and primer tail in SDA and tSDA primers).

Another aspect of the present invention is a method of detecting GBS by hybridizing at least one amplification primer comprising a target binding sequence to GBS nucleic acids, amplifying the GBS nucleic acids, and then detecting the amplified GBS nucleic acids. Preferred are species-specific (as defined above) methods of detecting GBS using an amplification primer(s). The amplification primer(s) hybridizes to, amplifies, and detects nucleic acids from the GBS3.1 sequence. Typically, the target sequence of the amplification primer will be double-stranded DNA of the GBS3.1 sequence of the GBS genome.

Preferably, the inventive methods disclosed herein employ a set of two or more amplification primers to amplify the GBS target sequences. Alternately, a single amplification primer can be used to carry out the present invention. A "primer set" comprises two or more primers that are designed or adapted to function together to amplify the target sequence. A primer set may only include amplification primers or it may also encompass bumper primers (e.g., for SDA and tSDA reactions). Preferably, the primer set includes two amplification primers for PCR or two amplification primers and two bumper primers for SDA/tSDA. As a further alternative, a primer set may contain one or more additional or alternate primers for carrying out the inventive methods. Amplification primers for use in carrying out the methods disclosed herein are as described hereinabove.

In one preferred embodiment of the invention, the amplification primers are hybridized to the GBS nucleic acids and extended. Amplification methods involving extension reactions include but are not limited to SDA and tSDA. Any amplification protocol which relies on cyclic, specific hybridization of primers to the target nucleic acid may be used, such as, PCR, SDA, tSDA, 3SR, the Qβ replicase system, or transcription based. Amplification by SDA and tSDA is preferred, with tSDA being more preferred.

The tSDA reactions can be carried out as described by U.S. Pat. No. 5,648,211 and European Application No. EP 0 684 315 to Frasier et al. Briefly, amplification by tSDA is based upon 1) the ability of a restriction endonuclease to nick the unmodified strand of a hemiphosphorothioate form of its double-stranded recognition site, and 2) the ability of certain polymerases to initiate replication at the nick and displace the downstream non-template strand. In tSDA reactions, the extension of primers, nicking of a hemi-modified restriction endonuclease recognition site, displacement of single-stranded extension products, annealing of primers to the extension products and subsequent extension of the primers occurs concurrently in the reaction mix. This is in contrast to PCR, in which the steps of the reaction occur in discrete phases or cycles as a result of the temperature cycling characteristics of the reaction.

Amplification reactions employing the primers of the present invention may incorporate thymine as disclosed by Walker et al. (*Proc. Nat'l Acad. Sci. USA* 89, 392 (1992); *Nucl. Acids. Res.* 20, 1691 (1992); both publications are herein incorporated by reference in its entirety), or they may wholly or partially substitute 2'-deoxyuridine 5'-triphosphate for TTP in the reaction to reduce cross-contamination with amplification products carried over from previous amplification reactions in reagents, pipetting devices and laboratory surfaces, for example, as is taught in European Pat. No. 0 624 643. Deoxyuridine (dU) is incorporated into amplification products and can be excised by treatment with uracil DNA glycosylase (UDG). These abasic sites render any contaminating amplification product unamplifiable in subsequent amplification reactions. UDG may be inactivated by UDG inhibitor prior to performing the subsequent amplification to prevent excision of dU in newly-formed amplification products.

In another preferred embodiment of the invention, amplification is carried out by hybridizing two or more amplification primers to the GBS nucleic acids, such that the primers are adjacent to each other when hybridized to their respective target sequences, and then ligating the hybridized amplification primers to produce a longer amplification product.

The presence of GBS or GBS nucleic acids is detected by determining the presence of the amplified GBS nucleic acids. Amplification products can be detected by hybridization to a labeled probe as described above. When a probe is used to detect amplification, the probe is typically selected to hybridize to a sequence that lies between the amplification primers (i.e., an internal probe). When amplification is performed by LCR, a probe that overlaps both primers and does not detect unligated primers may be used. Alternatively, amplification products may be detected by their characteristic size, for example by electrophoresis followed by ethidium bromide staining to visualize the nucleic acids species. This is the preferred method of detecting amplification products for LCR methods. In a further alternative, a labeled amplification primer is used. In a still further alternative, a labeled amplification primer/internal probe is extended on the target sequence (a detector primer) for detection of amplification products as described by Walker et al. *Proc. Nat'l Acad. Sci. USA* 89, 392 (1992); *Nucl. Acids. Res.* 20, 1691 (1992); both publications are herein incorporated by reference in its entirety.

Examples of specific detection methods that may be employed to detect amplification products include a chemiluminescent method in which amplified products are detected using a biotinylated capture probe and an enzyme-conjugated detector probe as described in U.S. Pat. No. 5,470,723. After hybridization of these two probes to different sites of the assay region of the target sequence (i.e., between the binding sites of the two amplification primers), the complex is captured on a streptavidin-coated microtiter plate, and the chemiluminescent signal is developed and read in a luminometer. As a further alternative method, a signal primer as described in European Pat. No. 0 678 582 is included in the amplification reaction to facilitate detection of the amplification product. According to this embodiment, labeled secondary amplification products are generated during amplification in a target amplification-dependentmanner and may be detected as an indication of target amplification by means of the associated label.

The present invention also provides kits for detecting GBS nucleic acids comprising a nucleic acid probe, amplification primer, preferably a pair of amplification primers or a primer set, each as described hereinabove. Species-specific methods, probes, amplification primers, and primer sets for detecting GBS, as described hereinabove, are preferred. The kit may optionally contain means for detecting the GBS nucleic acids using an oligonucleotide nucleic acid or amplification primer, as described hereinabove. Preferably, the oligonucleotide probe or amplification primer comprises at least 10 consecutive nucleotides of a GBS3.1 sequence. In an alternate embodiment, the amplification primer contains a sequence for amplification of a target nucleic acid in addition to a target binding sequence, each as described hereinabove. The kit may further include other components and reagents for performing the hybridization or amplification method (e.g., Southern hybridization, dot blot hybridization, PCR, SDA, etc., and the like). As an illustrative example, such a kit may contain at least one amplification primer according to the present invention. For detection by hybridization, a hybridization solution such as 25% formamide, 5×SSC, 5×Denhardt's solution, 100 µg/ml of single stranded DNA, and 5% dextran sulfate, or other reagents known to be useful for probe hybridization may also be included. See Sambrook et al., MOLECULAR CLONING, A LABORATORY MANUAL (2d ed. 1989); herein incorporated by reference in its entirety. Alternatively, reagents appropriate for use with one of the known nucleic acid amplification methods may be included with GBS3.1 amplification primers. The components of the kit are packaged together in a common container, typically including written instructions for performing selected specific embodiments of the methods disclosed herein. Components for detection methods, as described hereinabove, may optionally be included in the kit, for example, a second probe, and/or reagents and means for performing label detection (e.g., radiolabel, enzyme substrates, antibodies, etc., and the like).

The methods, probes, amplification primers, and kits disclosed herein can be used to detect GBS in any sample suspected of containing GBS. The samples may comprise isolated nucleic acids, isolated microorganisms, or they may be clinical samples. Typically, clinical samples are in the form of a biological fluid or tissue (e.g., milk, sputum, bronchial washings, gastric washings, blood, milk, lymph, skin, cerebrospinal and soft tissues). The samples may also be obtained by swabs, for example, vaginal or rectal swabs. As GBS infect both human and non-human animal species, the present invention is applicable to both human and veterinary diagnostic procedures and the sample may be obtained from either source.

The following Examples are provided to illustrate the present invention and should not be construed as limiting thereof.

EXAMPLE 1

Identification of a GBS-Specific DNA Fragment (GBS3.1)

Arbitrary primed polymerase chain reaction (AP-PCR) was used to create a differential display of amplification products from genomic DNA from 5 GBS and 9 non-GBS species (Table 1). The primers for AP-PCR were as follows:

Primer #27: 5' CCGGAACATCAGCAGCGA 3' (SEQ ID NO:1)

Primer #54: 5' CAGTGTACTGGATGCTCT 3' (SEQ ID NO:2)

The conditions for the amplification reactions are given below.
PCR Reaction Conditions (50 µl)
  10 mM Tris-HCl, pH 8.3 (at 25° C.)
  50 mM KCl
  1.5 mM MgCl$_2$
  0.001% (w/v) gelatin
  0.2 mM dNTPs
  0.2 µM $^{32}$P labeled primer #27
  0.2 µM $^{32}$P labeled primer #54
  5 ng genomic DNA from each strain as template
  2.5 U Taq DNA polymerase Gold™ (Perkin-Elmer)

The primers were 5' radiolabeled ($^{32}$P) according to the manufacturer's instructions (Random Primed DNA labeling Kit, Boehringer Mannheim).

The AP-PCR was carried out in a Perkin-Elmer Cetus thermocycler (Model 480), using the following amplification below.
PCR Profile

| | |
|---|---|
| 95° C. 3 minutes | Then change to: |
| 94° C. 1 minute | |
| 37° C. 1 minute | |
| 72° C. 2 minutes | |
| 35 Cycles | Then change to: |
| 4° C. overnight | |

Amplification products were isolated and visualized by electrophoresis through an 8% denaturing acrylamide gel (100 W) for 5 hours, followed by autoradiography (overnight exposure with Fuji medical X-Ray film).

A unique band was identified that was present in all GBS strains, but was absent in all non-GBS species tested. This band was designated "GBS3.1".

TABLE 1

Target organisms for Arbitrarily Primed Polymerase Chain Reaction

| Targets | ID# |
|---|---|
| GBS Ia | ATCC 12400 |
| GBS Ib | ATCC 12401 |
| GBS Ic | ATCC 25941 |
| GBS II | ATCC 12973 |
| GBS III | ATCC 12403 |
| Strep. Group A | ATCC 49399 |
| Strep. Group C | ATCC 12388 |
| Strep. Group D | ATCC 29212 |
| Strep. Group F | ATCC 12390 |
| Strep. Group G | ATCC 9106 |
| Strep. Pnemoniae | ATCC 27336 |
| Haemophilas influenza | ATCC 33533 |
| Neisseria gonorrhoeae | ATCC 23970 |
| Neisseria meningitidis | ATCC 13090 |

EXAMPLE 2

Re-Amplification of the GBS3.1 DNA Fragment by Arbitrarily Primed Polymerase Chain Reaction (AP-PCR)

The GBS3.1 band was excised from the gel, and the DNA was extracted by boiling the acrylamide gel slice in 100 µl of distilled sterile water for 15 minutes, followed by ethanol precipitation using glycogen as a carrier. Five µl of the extracted DNA was used to re-amplify the GBS3.1 band by AP-PCR using the primers from Example 1 (SEQ ID NO:1 and SEQ ID NO:2). The AP-PCR reaction conditions were as described in Example 1, with 5 µl of the extracted DNA being used in place of the 5 ng of template genomic DNA. The amplification profile was as given below.
PCR Profile

| | |
|---|---|
| 95° C. 2 minutes | Then change to: |
| 94° C. 1 minute | |
| 58° C. 1 minute | |
| 72° C. 2 minutes | |
| 35 Cycles | Then change to: |
| 4° C. overnight | |

Amplification products were isolated and visualized as described in Example 1. A PCR product of approximately 350 bp (as expected) was visible, representing the GBS3.1 fragment.

EXAMPLE 3

Cloning of the GBS3.1 Fragment

The re-amplified GBS3.1 fragment from Example 2 was cloned into the PCR TA II™ vector (Invitrogen; Carlsbad, Calif.) following the manufacturer's instructions. Bacterial cells were transformed with the pTA II™-GBS3.1 vector. The multiple cloning region of the pTA II™ vector has two Eco R1 sites flanking the insert, and the presence of the GBS3.1 fragment in transformed bacterial colonies was confirmed by Eco R1 digestion. The restriction digestion released a DNA fragment of approximately 350 base pairs in length, corresponding to the GBS3.1 fragment.

EXAMPLE 4

Sequencing of the GBS3.1 Fragment

The GBS3.1 DNA fragment cloned into the pTA II™ vector was sequenced using primers designed for the M13+ and SP6 Promoter regions of the vector. The ABI PRISM Terminator cycle sequencing kit (Perkin-Elmer) was used to cycle sequence GBS3.1 in a Perkin-Elmer Cetus Thermocycler (model 480) following the manufacturers' protocols. The amplified products were purified and run on an Applied Biosystems 373 DNA Sequencer. The GBS3.1 sequence from the type III GBS strain is shown in FIG. 1 (SEQ ID NO:3). No similar DNA sequence was found among over 800 sequence entries for Streptococcus species in GenBank.

EXAMPLE 5

Initial Screen of GBS3.1 for Species Specificity

Based on the sequence information obtained in Example 4, GBS3.1 specific PCR primers were designed, as shown below:

Sequences of PCR Primers

```
                                         (SEQ ID NO:4)
primer GBS3.1-5' 5' AAGCAATTCAGATCATTTTTCA 3'

(SEQ ID NO:5)
primer GBS3.1-3' 5' GAGATTAATTTTTGTTTATGAG 3'
```

Genomic DNA from 5 GBS strains and 10 non-GBS species were amplified using the GBS3.1 Primers. The PCR reaction conditions were the same as described in Example 1, with the exception that 50 ng of genomic DNA was used as template. The results are shown below in Table 2. All 5 of the GBS strains were successfully amplified by PCR using the GBS3.1-specific primers, while none of the non-GBS species showed any detectable amplification products. These initial results indicate that the GBS3.1 Primers exhibit complete specificity for GBS.

TABLE 2

Amplification of GBS Genomic DNA with the GBS3.1 Specific PCR Primers

| Strains amplified | ID# | Amplification |
|---|---|---|
| GBS Ia | ATCC 12400 | + |
| GBS Ib | ATCC 12401 | + |
| GBS Ic | ATCC 25941 | + |
| GBS II | ATCC 12973 | + |
| GBS III | ATCC 12403 | + |
| Strep. Group A | ATCC 49399 | − |
| Strep. Group C | ATCC 12388 | − |
| Strep. Group D | ATCC 29212 | − |
| Strep. Group F | ATCC 12390 | − |
| Strep. Group G | ATCC 9106 | − |
| Strep. Pnemoniae | ATCC 27336 | − |
| Strep. Pnemoniae | ATCC 6303 | − |
| Haemophilas influenza | ATCC 33533 | − |

TABLE 2-continued

Amplification of GBS Genomic DNA with the GBS3.1 Specific PCR Primers

| Strains amplified | ID# | Amplification |
|---|---|---|
| Neisseria gonorrhoeae | ATCC 23970 | − |
| Neisseria meningitidis | ATCC 13090 | − |

EXAMPLE 6

Specificity and Cross-Reactivity of the GBS3.1 PCR Primers

The PCR primers from Example 5 were used to further investigate the species specificity of the GBS3.1 fragment. Genomic DNA from 22 GBS strains and 40 non-GBS species were amplified using the GBS3.1 PCR primers. The PCR reaction conditions were as described in Example 1, with the exception that 50 ng of template genomic DNA was amplified in each reaction. The PCR amplification sequence was as shown below.

PCR Profile

| | |
|---|---|
| 95° C. 8 minutes | Then change to: |
| 94° C. 1 minute | |
| 58° C. 1 minute | |
| 72° C. 1 minute | |
| 45 Cycles | Then change to: |
| 4° C. overnight | |

The PCR amplification products were isolated and visualized by electrophoresis and autoradiography as described in Example 1. The results are shown below in Table 3. All of the GBS strains were amplified by the GBS3.1 primers, whereas none of the non-GBS species evaluated were amplified. These results indicate that the GBS3.1 Primers will identify all GBS strains, but will not cross-react with DNA from non-GBS species.

TABLE 3

Specificity and Cross-Reactivity of the GBS3.1 Specific PCR Primers

| | ID# | PCR Amplification |
|---|---|---|
| GBS Strains | | |
| GBS Ia | ATCC 12400 | + |
| GBS Ib | ATCC 12401 | + |
| GBS Ic | ATCC 25941 | + |
| GBS II | ATCC 12973 | + |
| GBS III | ATCC 12403 | + |
| GBS | 13813 | + |
| GBS | 747 | + |
| GBS | T-1964 | + |
| GBS | T-33 | + |
| GBS | T-35 | + |
| GBS | T-3282 | + |
| GBS | T-32 | + |
| GBS | T-31 | + |
| GBS | T-2887 | + |
| GBS | T-1952 | + |
| GBS | T-3863 | + |
| GBS | T-37 | + |
| GBS | 12040 | + |
| GBS | AAAII | + |
| GBS | 4768 | + |
| GBS | 6638 | + |
| GBS | 11586 | + |

TABLE 3-continued

Specificity and Cross-Reactivity of the GBS3.1 Specific PCR Primers

|  | ID# | PCR Amplification |
|---|---|---|
| Non-GBS Species | | |
| Strep. Group A | ATCC 49399 | − |
| Strep. Group C | ATCC 12388 | − |
| Strep. Group C | 152 | − |
| Strep. Group D | ATCC 29212 | − |
| Strep. Group F | ATCC 12390 | − |
| Strep. Group G | ATCC 9106 | − |
| Strep. Anginosus | ATCC 27335 | − |
| Strep. Bovis | ATCC 33317 | − |
| Strep. Pnemoniae | ATCC 6303 | − |
| Strep. Pnemoniae | ATCC 27336 | − |
| Non-GBS Species Tested in 8 Pools | | |
| Acinetobacter lwoffi | ATCC 19901 | − |
| Branhamella catarrhlis | ATCC 25240 | − |
| Candida albicans | ATCC 44808 | − |
| Chlamydia trachomatis | LGV-2 | − |
| Chlamydia trachomatis | J | − |
| Chlamydia trachomatis | | − |
| Gardnerella vaginalis | ATCC 14018 | − |
| Haemophilas influenza | ATCC 33533 | − |
| Kingella kingae | ATCC 23330 | − |
| Klebsiella pneumoniae | ATCC 13883 | − |
| Moraxella lacunata | ATCC 17967 | − |
| Mycoplasma orale | ATCC 23714 | − |
| Neisseria cinerea | ATCC 14685 | − |
| Neisseria elongata | ATCC 25295 | − |
| Neisseria flavescens | ATCC 13120 | − |
| Non-GBS/Pooled | | |
| Neisseria gonorrhoeae | ATCC 19424 | − |
| Neisseria gonorrhoeae | ATCC 35541 | − |
| Neisseria gonorrhoeae | BDMS 2900 | − |
| Neisseria gonorrhoeae | BDMS 1632 | − |
| Neisseria lactamica | ATCC 44418 | − |
| Neisseria lactamica | ATCC 49142 | − |
| Neisseria meningitidis | ATCC 13077 | − |
| Neisseria meningitidis | ATCC 13090 | − |
| Neisseria mucosa | ATCC 19696 | − |
| Neisseria sicca | ATCC 29193 | − |
| Neisseria subflava | ATCC 14799 | − |
| Proteus mirabilis | ATCC 29906 | − |
| Staph. aureus | ATCC 12598 | − |
| Salmonella minnesota | ATCC 9700 | − |
| Tricomonas vaginalis | ATCC 30001 | − |

EXAMPLE 7

Sequencing of the GBS3.1 Fragment from Fifteen GBS Strains

To determine the degree of sequence homology in the GBS3.1 sequence across GBS strains, the GBS3.1 specific primers were used amplify and cycle sequence the GBS3.1 fragment from fifteen of the GBS strains studied in Example 6. The 15 GBS strains used for sequencing are shown in Table 4. The PCR amplification products from Example 6 were purified using the Qiagen Qiaex II system according to the manufacturer's instructions. Each purified amplified DNA fragment was used as a template for cycle sequencing as described in Example 4. The DNA fragments were sequenced using the GBS3.1 specific primers (GBS3.1-5' and GBS3.1–3') as shown in Example 5.

Figure 2B:
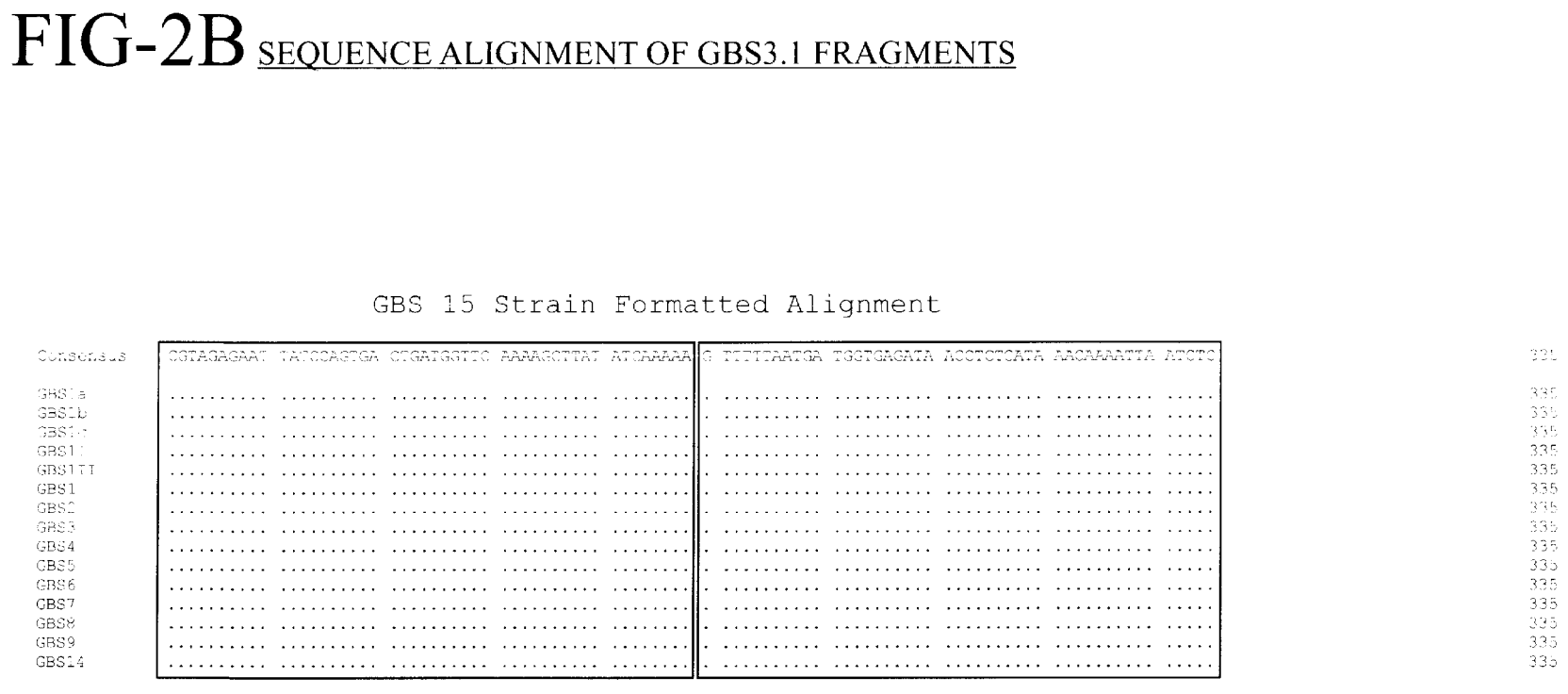

The GBS3.1 sequences from the 15 GBS strains are shown in FIG. 2. The sequences were aligned and a consensus GBS3.1 sequence (SEQ ID NO:6) determined, as shown in FIG. 2. The 15 GBS strains represented 4 different GBS3.1 sequences (SEQ ID NO:3, SEQ ID NO:7, SEQ ID NO:8, and SEQ ID NO:9). Only 3 base variants among the sequences were identified along a total length of 336 base pairs, indicating a homology of >99%.

TABLE 4

GBS Strains for Sequencing GBS3.1

| GBS Strains | ID# |
|---|---|
| GBS Ia | ATCC 12400 |
| GBS Ib | ATCC 12401 |
| GBS Ic | ATCC 25941 |
| GBS II | ATCC 12973 |
| GBS III | ATCC 12403 |
| GBS | 13813 |
| GBS | 747 |
| GBS | T-1964 |
| GBS | T-33 |
| GBS | T-35 |
| GBS | T-3282 |
| GBS | T-32 |
| GBS | T-31 |
| GBS | T-2887 |
| GBS | AAAII |

EXAMPLE 8

Thermophilic Strand Displacement Amplification (tSDA) Procedure

The tSDA reactions were carried out essentially as previously described in U.S. Pat. No. 5,648,211 and European Application No. EP 0 684 315 to Frasier et al., with substitution of dUTP for TTP to allow for inactivation (decontamination) of amplicons carried over to subsequent reactions using uracil DNA glycosylase (UDG).

For each tSDA reaction, the target DNA was added to a tube containing human placental DNA, DMSO, glycerol, and potassium phosphate. The reaction mixture was boiled for two minutes to denature the DNA and then transferred to a Thermal-lok set at 45° C. The decontamination mix containing potassium phosphate, dGTP, dATP, thio-dCTP, primers, bumpers, BSA, DTT, trehalose, UDG, and magnesium acetate was then added and the mixture incubated for 30 minutes at 45° C. Following the incubation, the amplification mix containing potassium phosphate, dUTP, BSA, DTT, trehalose, UDI, Bso B1, Bst polymerase, and magnesium acetate was added, and the tube incubated at the amplification temperature for 30 minutes. The amplification reaction was stopped by boiling the reaction tube for 5 minutes. This protocol was used in all experiments.

tSDA Final Reaction Mixture (50 μl)

45 mM Potassium phosphate

100 μg/ml acetylated bovine serum albumin 1.4 mM thiodCTP, 0.5 mM dUTP, 0.2 mM dGTP, and 0.2 mM dATP 6 mM Magnesium Acetate 0.5 μM and 0.05 μM of tSDA primers and bumpers, respectively 650 ng per reaction of human placental DNA 7% Glycerol

7% DMSO 9 units of Bst polymerase 160 units of Bso B1

1 unit Uracil-N-glycosylase 5 units Uracil-N-glycosylase inhibitor

Temperature: 52° C.

The amplification products are detected with an amplicon specific radiolabeled detection probe in a primer extension reaction as described below in Example 9. Alternatively, the amplification products can be detected by a latex-immunoassay, in which one detector probe is biotinylated and the second is antigen conjugated.

EXAMPLE 9

Radiolabel Extension Reactions

The detection probes were 5'-$^{32}$P-labeled using T4 polykinase to facilitate detection of amplification product. The radiolabeling conditions were: 1 mM detector probe oligonucleotide, 30 units T4 DNA polynucleotide kinase, 70 μCi γ-$^{32}$P-ATP, and 1×PNK buffer (10×PNK buffer available from United States Biochemical, Inc.). The reactions were allowed to proceed at 37° C. for 45 minutes, and were stopped by heating the samples at 65° C. for 10 minutes. The labeled detection probe was stored at −20° C. and used within one week.

The radiolabel extension reactions were carried out by mixing 5 μl of the tSDA sample with 5 μl of the detection mix containing the radiolabeled detection probe (detection mix=50 mM KPO$_4$, 0.2 mM each α-thio-dATP, dCTP, and dGTP, 0.5 mM dUTP, and 1 μl radiolabeled detection probe). The samples were boiled for 2 minutes, followed by at least 2 minutes of equilibration in a 37° C. waterbath. Enzyme mix (1 μl) was added to each detection reaction and incubated at 37° C. for 10 minutes (enzyme mix=2 units exo-Klenow and 1×React 1 buffer (10×React 1 buffer available from BRL Life Technologies Inc.). Reactions were stopped by the addition of 10 μl stop mix (available from USB; 3×=95% formamide, 20 mM EDTA, 0.05% bromophenol blue, 0.05% xylene cyanol), followed by boiling the samples for 2 minutes. Radiolabeled extension products were detected by separating the reaction products through an 8% polyacrylamide gel followed by autoradiography and quantification with a Molecular Dynamics 455SI phosphoimager and ImageQuant v1.1 software.

EXAMPLE 10

Amplification of GBS3.1 by Thermophilic Strand Displacement Amplification (tSDA)

GBS3.1 specific amplification primers, bumpers, and detection probes were designed for thermophilic Strand Displacement Amplification (tSDA) of GBS3.1 as shown in FIG. 3A. The tSDA primers were directed to a subregion at the 5' half of GBS3.1 fragment. The Bso B1 restriction site in each primer is italicized and the specific binding site underlined. All of the amplification primer combinations (3 left primers×3 right primers) were screened. Positive amplification was observed with all 9 Primer combinations. The best results were observed with the primer combination GBS3.1ALM48 (SEQ ID NO:10) and GBS3.1AR46 (SEQ ID NO:13), which was selected for further investigation. The bumpers were GBS3.1BL44 (SEQ ID NO:16) and GBS3.1BR44 (SEQ ID NO:17) and the detectors were GBS3.1D40 (SEQ ID NO:18), GBS3.1DR46 (SEQ ID NO:19), and GBS.1C42 (SEQ ID NO:20) as shown in FIG. 3A. The selected GBS3.1 tSDA system is depicted in FIG. 3B. The amplification product is 61 bp in length.

EXAMPLE 11

Sensitivity of the GBS3.1 tSDA System

A genome titration curve was performed to determine the minimum genome copy number that could be amplified and detected by the GBS3.1 tSDA system. GBS genomic DNA was isolated and diluted in 10 ng of human placental DNA. tSDA reactions were performed as described in Example 8 using $10^5$, $10^4$, $10^3$, $10^2$, $10^1$ and 0 genome copies per reaction. A sensitivity of 10 genome copies was achieved with all detection systems.

Example 12

Specificity and Cross-reactivity of the GBS3.1 tSDA System

An experiment was carried out to evaluate the specificity and cross-reactivity of the GBS3.1 tSDA system. Genomic DNA (both lysate and clean preparations) from 33 GBS strains were tested with the GBS3.1 tSDA system for specificity (Table 4). Pooled samples from 67 non-GBS species were tested for cross-reactivity (Table 5). Pooled genomic DNA from three to five non-GBS species, each at the $10^7$ genome level, was pipetted into one tube and amplified using the GBS3.1 tSDA system from Example 9. The amplification primers, bumpers and detector were as follows:

Primer/Bumper Set: GBS3.1AL48, GBS3.1AR46, GBS3.1BL44, GBSBR44 Detector: GBS3.1DR46

To prevent false negatives arising due to amplification inhibition, a control sample was included that contained the cross-reactive pool with 2×$10^4$ genome copies of GBS template added. Sixteen such pools and their related controls (spikes) were tested. All 33 GBS strains were positive, and all of the pools containing the 67 non-GBS species were negative (except in the control pools containing GBS spikes).

TABLE 5

GBS Strains Showing Positive Amplification by the GBS3.1 tSDA System

| Type | ID# |
|---|---|
| Ia | 265 |
| Ia | 694 |
| Ia | 836 |
| Ia | 926 |
| Ia | 781 |
| Ib | 848 |
| Ib | 861 |
| Ib | 883 |
| Ib | 900 |
| Ib | 1088 |
| Ic | 575 |
| Ic | 580 |
| Ic | 597 |
| Ic | 598 |
| Ic | 607 |
| II | 235 |
| II | 800 |
| II | 910 |
| II | 934 |
| II | 1004 |
| III | 749 |
| III | 771 |
| III | 775 |
| III | 843 |
| III | 879 |
| IV | 3139 |
| V | 721 |
| V | 753 |
| V | 874 |
| V | 940 |
| V | 950 |
| VI | SS1214 |
| VII | PT7274 |

TABLE 6

Amplification of non-GBS Species
(in 16 pools) by the GBS3.1 tSDA System

| Pool | Non-GBS Species |
|---|---|
| Pool A | Strep. Group A 12901, Strep. Group A 12902, Strep. Group A 18, Strep. Group A 195J, Strep. Group A 400 |
| Pool C + D | Strep. Group C 163, Strep. Group C 2164, Strep. Group C 12388, Strep. Group D 29212 |
| Pool F | Strep. Group F 12393, Strep. Group F 77, Strep. Group F 110, Strep. Group F 114 |
| Pool G: | Strep. Group G R582336, Strep. Group G 165, Strep. Group G 12394 |
| Pool 1 | Strep. pnemoniae 12, Strep. pnemoniae 184J, Strep. pnemoniae 628, Strep. pnemoniae III, Strep. pnemoniae SPA18 |
| Pool 2 | Strep. uberis 19436, Strep. equinis 9812, Strep. parasanguis 15909 |
| Pool 3 | Strep. constellatus 3483, Strep. gallinarum 35539, Strep. intermedius 8850, Strep. salivarius 461 |
| Pool 4 | Salmonella minnesota 9700, Salmonella typhimurium 13311, E. coli 11775, Klebsiella pneumoniae 13883 |
| Pool 5 | Acinetobacter lwoffi 19901, Haemophilas influenza 33533, Moraxella lacunata 17967, Proteus mirabilis 29906 |
| Pool 6 | Candida albicans 44808, Gardnerella vaginalis 14018, Mycoplasma orale 23714, Tricomonas vaginalis 30001 |
| Pool 7 | Staph. aureus 12598, HSV-1, HSV-2, Peptostreptococcus productus 27340 |
| Pool 8 | Neisseria cinerea 14685, Neisseria elongata 25295, Neisseria flavescens 13120, Neisseria sicca 29193, Neisseria lactamica 44418 |
| Pool 9 | Branhamella catarrhlis 25240, Kingella kingae 23330, Neisseria mucosa 19696, Neisseria subflava 14799 |
| Pool 10 | Neisseria meningitidis 13077, Neisseria meningitidis 13102, Neisseria meningitidis 13113, Neisseria meningitidis 14632, Neisseria meningitidis 35559 |
| Pool 11 | Neisseria gonorrhoeae 19424, Neisseria gonorrhoeae 35541, Neisseria gonorrhoeae BDMS 2900, Neisseria gonorrhoeae BDMS 1632 |
| Pool 12 | Chlamydia trachomatis LGV-2, Chlamydia trachomatis J, Chlamydia pneumoniae, Chlamydia psittaci |

EXAMPLE 13

Summary of the GBS3.1 Fragment

1. The GBS3.1 fragment is approximately 336 bp in length.

2. The 15 sequenced GBS strains share >99% homology in the GBS3.1 sequence.

3. No Bso B1 restriction site was found in the fragment.

4. No similar DNA sequence was found among over 800 sequence entries of Streptococcus species in GenBank.

5. PCR specificity tests of 22 GBS strains were 100% positive.

6. PCR cross-reactivity tests of 43 non-GBS species were 100% negative.

7. tSDA specificity tests of 33 GBS strains (including type I to type VII) were 100% positive.

8. tSDA cross-reactivity tests of 67 non-GBS species were 100% negative.

9. The sensitivity of the GBS3.1 tSDA system was 10 genomes.

All patents and patent publications are herein incorporated by reference in their entirety, as if each individual patent or patent publication was specifically and individually indicated to be incorporated by reference.

Although the foregoing invention has been described in some detail by way of illustration and example for purposes of clarity and understanding, it will be obvious that certain changes and modifications may be practiced within the scope of the appended claims.

That which is claimed is:

1. A method for species-specific detection of *Streptococcus agalactiae* nucleic acids comprising:
    (a) hybridizing an oligonucleotide probe to *Streptococcus agalactiae* nucleic acids, the probe consisting of at least 10 consecutive nucleotides of a *Streptococcus agalactiae* GBS3.1 sequence, said *Streptococcus agalactiae* GBS3.1 sequence selected from the group consisting of SEQ ID NO:3, SEQ ID NO:6, SEQ ID NO:7, SEQ ID NO:8 and SEQ ID NO:9; and then
    (b) detecting hybridization between the oligonucleotide probe and the *Streptococcus agalactiae* nucleic acids.

2. A method according to claim 1, wherein the oligonucleotide probe is 10–50 nucleotides long.

3. A method according to claim 1, wherein the oligonucleotide probe is selected from the group consisting of SEQ ID NO:4, SEQ ID NO:5, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, the target binding sequence of SEQ ID NO:15, SEQ ID NO:16, SEQ ID NO:17, SEQ ID NO:18, SEQ ID NO:19, and SEQ ID NO:20.

4. A method according to claim 1, wherein said detecting is carried out by detecting a detectable label bound to the oligonucleotide probe.

5. A method for species-specific detection of *Streptococcus agalactiae* nucleic acids comprising:
    (a) hybridizing to *Streptococcus agalactiae* nucleic acids at least one amplification primer comprising a target binding sequence, the target binding sequence consisting of at least 10 consecutive nucleotides of a *Streptococcus agalactiae* GBS3.1 sequence, said *Streptococcus agalactiae* GBS3.1 sequence selected from the group consisting of SEQ ID NO:3, SEQ ID NO:6, SEQ ID NO:7, SEQ ID NO:8 and SEQ ID NO:9; and
    (b) amplifying the *Streptococcus agalactiae* nucleic acids with the at least one amplification primer; and then
    (c) detecting the amplified *Streptococcus agalactiae* nucleic acids.

6. A method according to claim 5, wherein said amplifying is carried out by extending the at least one hybridized amplification primer.

7. A method according to claim 5, wherein the at least one amplification prime further comprises a specialized sequence which does not hybridize to *Streptococcus agalactiae* nucleic acids and is necessary for amplification of the *Streptococcus agalactiae* nucleic acids.

8. A method according to claim 5, wherein the target binding sequence of the at least one amplification primer is selected from the group consisting of SEQ ID NO:4, SEQ ID NO:5, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, the target binding sequence of SEQ ID NO:15, SEQ ID NO:16, SEQ ID NO:17, SEQ ID NO:18, SEQ ID NO:19, and SEQ ID NO:20.

9. A method according to claim 5, wherein the at least one amplification primer is selected from the group consisting of SEQ ID NO:10, SEQ ID NO:11, SEQ ID NO:12, SEQ ID NO:13, SEQ ID NO:14, and SEQ ID NO:15.

10. A method according to claim 5, wherein said detecting is conducted with a probe which is selected from the group consisting of SEQ ID NO:18, SEQ ID NO:19, and SEQ ID NO:20.

11. A method according to claim 5, wherein said hybridizing comprises hybridizing a first amplification primer having a sequence as given in SEQ ID NO:4 and a second amplification primer having a sequence as given in SEQ ID NO:5 to the *Streptococcus agalactiae* nucleic acids.

12. A method for species-specific detection of *Streptococcus agalactiae* nucleic acids comprising:
    (a) hybridizing to *Streptococcus agalactiae* nucleic acids a first and a second amplification primer; each of the first and second amplification primers comprising a target binding sequence and a specialized sequence which does not hybridize to *Streptococcus agalactiae* nucleic acids and is necessary for amplification of *Streptococcus agalactiae* nucleic acids wherein the target binding sequence of the first amplification primer is selected from the group consisting of the target binding sequences of SEQ ID NO:10, SEQ ID NO:11, and SEQ ID NO:12, and wherein the target binding sequence of the second amplification primer is selected from the group consisting of the target binding sequences of SEQ ID NO:13, SEQ ID NO:14 and SEQ ID NO:15; and (b) extending the hybridized first and second amplification primers on the *Streptococcus agalactiae* target nucleic acids, whereby the target nucleic acid is amplified; and then (c) detecting the amplified *Streptococcus agalactiae* nucleic acids.

13. A method according to claim 12, wherein the first amplification primer is selected from the group consisting of SEQ ID NO:10, SEQ ID NO:11 and SEQ ID NO:12, and wherein the second amplification primer is selected from the group consisting of SEQ ID NO:13, SEQ ID NO:14, and SEQ ID NO:15.

14. A method according to claim 13, wherein the first amplification primer is SEQ ID NO:10 and the second amplification primer is SEQ ID NO:13.

15. A method according to claim 12, wherein said detecting is carried out with a detector probe selected from the group consisting of SEQ ID NO:18, SEQ ID NO:19, and SEQ ID NO:20.

16. A method according to claim 12, wherein said hybridizing further comprises hybridizing a first and a second bumper primer to the *Streptococcus agalactiae* nucleic acids, the first bumper primer consisting of SEQ ID NO:16 and the second bumper primer consisting of SEQ ID NO:17.

17. An isolated DNA consisting of a *Streptococcus agalactiae* GBS3.1 sequence, said *Streptococcus agalactiae* GBS3.1 sequence selected from the group consisting of SEQ ID NO:3, SEQ ID NO:6, SEQ ID NO:7, SEQ ID NO:8 and SEQ ID NO:9.

18. An oligonucleotide comprising a target binding sequence consisting of at least 10 consecutive nucleotides of the isolated DNA of claim 17.

19. An oligonucleotide according to claim 18, wherein said oligonucleotide is 10–75 nucleotides long.

20. An oligonucleotide according to claim 18, wherein said oligonucleotide is 15–50 nucleotides long.

21. An oligonucleotide according to claim 18, wherein said oligonucleotide is selected from the group consisting of SEQ ID NO:4, SEQ ID NO:5, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, and the target binding sequence of SEQ ID NO:15, SEQ ID NO:16, SEQ ID NO; 17, SEQ ID NO:18, SEQ ID NO:19, and SEQ ID NO:20.

22. An oligonucleotide according to claim 18, wherein said oligonucleotide further comprises a specialized sequence which does not hybridize to *Streptococcus agalactiae* nucleic acids and is necessary for amplification of *Streptococcus agalactiae* nucleic acids.

23. An oligonucleotide according to claim 22, wherein said oligonucleotide is selected from the group consisting of SEQ ID NO:10, SEQ ID NO:11, SEQ ID NO:12, SEQ ID NO:13, SEQ ID NO:14, and SEQ ID NO:15.

24. A primer set for species-specific amplification of *Streptococcus agalactiae* nucleic acids comprising a first amplification primer comprising a target binding sequence consisting of at least 10 consecutive nucleotides of an isolated DNA according to claim 17.

25. A primer set according to claim 24, wherein said first amplification primer is selected from the group consisting of SEQ ID NO:4, SEQ ID NO:5, the target binding sequence of SEQ ID NO:10, the target binding sequence of SEQ ID NO:11, the target binding sequence of SEQ ID NO:12, the target binding sequence of SEQ ID NO:13, the target binding sequence of SEQ ID NO:14, and the target binding sequence of SEQ ID NO:15, SEQ ID NO:16, SEQ ID NO:17, SEQ ID NO:18, SEQ ID NO:19, SEQ ID NO:20.

26. A primer set according to claim 25, wherein said first amplification primer is SEQ ID NO:4 and a second amplification primer is SEQ ID NO:5.

27. A primer set according to claim 24, wherein said first amplification primer further comprises a specialized sequence which does not hybridize to *Streptococcus agalactiae* nucleic acids and is necessary for amplification of the *Streptococcus agalactiae* nucleic acids.

28. A primer set according to claim 27, wherein said first amplification primer is selected from the group consisting of SEQ ID NO:10, SEQ ID NO:11, SEQ ID NO:12, SEQ ID NO:13, SEQ ID NO:14, and SEQ ID NO:15.

29. A primer set according to claim 28 further comprising a first bumper primer having a sequence consisting of SEQ ID NO:16 and a second bumper primer having a sequence consisting of SEQ ID NO:17.

30. A primer set according to claim 28, wherein said first amplification primer is selected from the group consisting of SEQ ID NO:10, SEQ ID NO:11, SEQ ID NO:12 and a second amplification primer is selected from the group of SEQ ID NO:13, SEQ ID NO:14, and SEQ ID NO:15.

31. A primer set according to claim 30, wherein said first amplification primer is SEQ ID NO:10 and said second amplification primer is SEQ ID NO:13.

32. A set of primers according to claim 30, wherein said first and second amplification primers are contained in a common aqueous solution.

33. A primer set for species-specific amplification of *Streptococcus agalactiae* nucleic acids comprising a first amplification primer consisting of SEQ ID NO:10, a second amplification primer consisting of SEQ ID NO:13, a first bumper primer consisting of SEQ ID NO:16, and a second bumper primer consisting of SEQ ID NO:17.

34. A kit for species-specific detection of *Streptococcus agalactiae* nucleic acids comprising:

(a) an oligonucleotide according to claims 18 or 22; and (b) means for detecting said *Streptococcus agalactiae* nucleic acids.

35. A kit for species-specific detection of *Streptococcus agalactiae* nucleic acids comprising:

(a) a set of primers for species-specific detection of *Streptococcus agalactiae* nucleic acids according to claims 24 or 27; and (b) means for detecting said *Streptococcus agalactiae* nucleic acids.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:1:

CCGGAACATC AGCAGCGA                                  18

(2) INFORMATION FOR SEQ ID NO:2:

(i) SEQUENCE CHARACTERISTICS:
      (A) LENGTH: 18 base pairs
      (B) TYPE: nucleic acid

```
        (C) STRANDEDNESS: single
        (D) TOPOLOGY: linear (ii) MOLECULE TYPE: other nucleic acid (xi) SEQUENCE DESCRIPTION: SEQ ID NO:2:

CAGTGTACTG GATGCTCT                                                      18

(2) INFORMATION FOR SEQ ID NO:3:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: GBS
        (B) STRAIN: GBSIa, GBSIII and GBS9

(xi) SEQUENCE DESCRIPTION: SEQ ID NO:3:

AAGCAATTCA GATCATTTTT CAGTAACGGT GGAACGTTTA CCTAGAACCC ATTATACTGC          60

TAGCCTTGAA GGGACTAGTG ACGGAAAAGA GATTAAACTC AAAAAAGATT ATGATGGTAA         120

AAACCAAACT ATTGATTTAT CGGTCGCTTT TAAATCTTTT ACAGTAACAA GTAATCTTAT         180

GGATGGTAAT CTTTATTTTG GTGATAATCG TATTGCTAAA TTAAAAGATG GTAGCTATTC         240

CGTAGAGAAT TATCCAGTGA CTGATGGTTC AAAAGCTTAT ATCAAAAAAG TTTTTAATGA         300

TGGTGAGATA ACCTCTCATA AACAAAAATT AATCTC                                  336

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

AAGCAATTCA GATCATTTTT CA                                                 22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

GAGATTAATT TTTGTTTATG AG                                                 22

(2) INFORMATION FOR SEQ ID NO:6:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
```

(A) ORGANISM: GBS (xi) SEQUENCE DESCRIPTION: SEQ ID NO:6:

AAGCAATTCA GATCATTTTT CAGTAACGGT GGAACGTTTA CCTAGAACCY ATTATACTGC    60

TAGCCTTGAA GGGACTAGTG ACGGAAAAGA GATTAAACTC AAAAAAGATT ATGATGGTAA   120

AAACCAAACT ATTGATTTAT CGGTCGCTTT TAAATCTTTT ACAGTAACAA GTAATCTTAT   180

GGATGGTAAT CTTTATTTTG GTGATAATCG TATTGCTAAA TTAAAAGATG GTAGCYATTC   240

CGTAGAGAAT TATCCAGTGA CTGATGGTTC AAAAGCTTAT ATCAAAAARG TTTTTAATGA   300

TGGTGAGATA ACCTCTCATA AACAAAAATT AATCTC                            336

(2) INFORMATION FOR SEQ ID NO:7:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: GBS
        (B) STRAIN: GBSIb, GBSIc, GBS1, GBS4, and GBS5

(xi) SEQUENCE DESCRIPTION: SEQ ID NO:7:

AAGCAATTCA GATCATTTTT CAGTAACGGT GGAACGTTTA CCTAGAACCC ATTATACTGC    60

TAGCCTTGAA GGGACTAGTG ACGGAAAAGA GATTAAACTC AAAAAAGATT ATGATGGTAA   120

AAACCAAACT ATTGATTTAT CGGTCGCTTT TAAATCTTTT ACAGTAACAA GTAATCTTAT   180

GGATGGTAAT CTTTATTTTG GTGATAATCG TATTGCTAAA TTAAAAGATG GTAGCTATTC   240

CGTAGAGAAT TATCCAGTGA CTGATGGTTC AAAAGCTTAT ATCAAAAAGG TTTTTAATGA   300

TGGTGAGATA ACCTCTCATA AACAAAAATT AATCTC                            336

(2) INFORMATION FOR SEQ ID NO:8:

(i) SEQUENCE CHARACTERISTICS:
        (A) LENGTH: 336 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: GBS
        (B) STRAIN: GBSII (xi) SEQUENCE DESCRIPTION: SEQ ID NO:8:

AAGCAATTCA GATCATTTTT CAGTAACGGT GGAACGTTTA CCTAGAACCT ATTATACTGC    60

TAGCCTTGAA GGGACTAGTG ACGGAAAAGA GATTAAACTC AAAAAAGATT ATGATGGTAA   120

AAACCAAACT ATTGATTTAT CGGTCGCTTT TAAATCTTTT ACAGTAACAA GTAATCTTAT   180

GGATGGTAAT CTTTATTTTG GTGATAATCG TATTGCTAAA TTAAAAGATG GTAGCTATTC   240

CGTAGAGAAT TATCCAGTGA CTGATGGTTC AAAAGCTTAT ATCAAAAAGG TTTTTAATGA   300

TGGTGAGATA ACCTCTCATA AACAAAAATT AATCTC                            336

(2) INFORMATION FOR SEQ ID NO:9:

(i) SEQUENCE CHARACTERISTICS:
        (A) LENGTH: 336 base pairs
        (B) TYPE: nucleic acid

```
        (C) STRANDEDNESS: double
        (D) TOPOLOGY: linear (ii) MOLECULE TYPE: DNA (genomic)

(vi) ORIGINAL SOURCE:
         (A) ORGANISM: GBS
         (B) STRAIN: GBS2, GBS3, GBS6, GBS7, GBS8, GBS14

(xi) SEQUENCE DESCRIPTION: SEQ ID NO:9:

AAGCAATTCA GATCATTTTT CAGTAACGGT GGAACGTTTA CCTAGAACCC ATTATACTGC      60

TAGCCTTGAA GGGACTAGTG ACGGAAAAGA GATTAAACTC AAAAAAGATT ATGATGGTAA     120

AAACCAAACT ATTGATTTAT CGGTCGCTTT TAAATCTTTT ACAGTAACAA GTAATCTTAT     180

GGATGGTAAT CTTTATTTTG GTGATAATCG TATTGCTAAA TTAAAAGATG GTAGCCATTC     240

CGTAGAGAAT TATCCAGTGA CTGATGGTTC AAAAGCTTAT ATCAAAAAAG TTTTTAATGA     300

TGGTGAGATA ACCTCTCATA AACAAAAATT AATCTC                              336

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

CGATTCCGCT CCAGACTTCT CGGGAGTAAC GGTGGAACGT                            40

(2) INFORMATION FOR SEQ ID NO:11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

CGATTCCGCT CCAGACTTCT CGGGAGTAAC GGTGGAACG                             39

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

CGATTCCGCT CCAGACTTCT CGGGAGTAAC GGTGGAAC                              38

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:
```

ACCGCATCGA ATGCATGTCT CGGGGTCACT AGTCCCTTCA                40

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

ACCGCATCGA ATGCATGTCT CGGGGTCACT AGTCCCTTC                 39

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

ACCGCATCGA ATGCATGTCT CGGGTCACTA GTCCCTTCA                 39

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:16:

AAGCAATTCA GATCATT                                         17

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

TTTGAGTTTA ATCTCTTT                                        18

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:18:

GTTTACCTAG AACC                                            14

(2) INFORMATION FOR SEQ ID NO:19:

```
    (i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:19:

TGGGTTCTAG GTAAAC                                                      16

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

TTATACTGCT AGCCT                                                       15
```